(12) United States Patent
Bulliard et al.

(10) Patent No.: US 6,794,525 B2
(45) Date of Patent: Sep. 21, 2004

(54) OPTICALLY ACTIVE CHIRAL DIPHOSPHINE LIGANDS

(75) Inventors: Michel Bulliard, Angers (FR); Blandine Laboue, Angrie (FR); Sonia Roussiasse, Ecouflant (FR)

(73) Assignee: PPG-SIPSY (FR)

(*) Notice: Subject to any disclaimer, the term of this patent is extended or adjusted under 35 U.S.C. 154(b) by 0 days.

(21) Appl. No.: 10/356,233

(22) Filed: Jan. 31, 2003

(65) Prior Publication Data
US 2003/0195369 A1 Oct. 16, 2003

Related U.S. Application Data

(63) Continuation of application No. PCT/FR01/02550, filed on Aug. 3, 2001.

(30) Foreign Application Priority Data
Aug. 3, 2000 (FR) .............................. 00 10269

(51) Int. Cl.$^7$ ............................. C07F 15/00; C07F 9/02; B01J 31/00
(52) U.S. Cl. ................. 556/22; 556/23; 568/8; 502/170; 502/171; 502/169; 585/250; 585/275
(58) Field of Search .................... 556/22, 23; 568/8, 568/17; 502/169, 170, 171; 585/250, 275

(56) References Cited
FOREIGN PATENT DOCUMENTS

| EP | 0 647 648 A1 | 4/1995 |
|----|--------------|--------|
| EP | 1 002 801 A1 | 5/2000 |
| WO | WO 93/15089  | 8/1993 |
| WO | WO 93/15090  | 8/1993 |
| WO | WO 01/21625 A1 | 3/2001 |

*Primary Examiner*—Porfirio Nazario-Gonzalez
(74) *Attorney, Agent, or Firm*—Piper Rudnick LLP

(57) ABSTRACT

An (R) or (S) chiral diphosphine of formula (I):

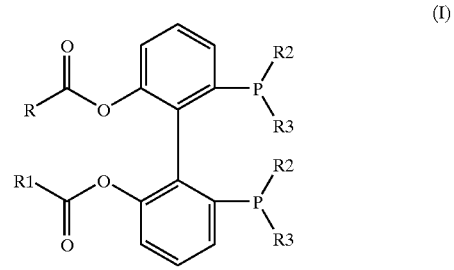

wherein R and R1, which can be identical or different, represent an optionally saturated $C_{1-10}$ alkyl group, an optionally saturated $C_{3-9}$ cycloalkyl group, a $C_{5-10}$ aryl group, the groups being optionally substituted by a halogen, a hydroxy, a $C_{1-5}$ alkoxy, an amino, a sulfino, a sulonfyl, with $R_4$ representing an alkyl, an alkoxy or an alkylcarbonyl, the alkyl, cycloalkyl, aryl groups optionally including one or more heteroatoms, or R and R1 together represent an optionally saturated $C_{2-6}$ substituted alkyl group, an optionally saturated $C_{3-9}$ cycloalkyl group, a $C_{5-10}$ aryl group, the cycloalkyl or aryl groups being optionally substituted by a $C_{1-5}$ alkyl, a halogen, a hydroxy, a $C_{1-5}$ alkoxy, an amino, a sulfino, a sulonfyl, with $R_4$ representing an alkyl, an alkoxy or an alkylcarbonyl, the alkyl, cycloalkyl, aryl groups optionally including one or more heteroatoms, R2 and R3, which can be identical or different, represent an optionally saturated $C_{3-8}$ cycloalkyl group, a $C_{6-10}$ aryl group, the groups being optionally substituted by a halogen, a hydroxy, a $C_{1-5}$ alkoxy, an amino, a sulfino, a sulonfyl, with $R_4$ representing an alkyl, an alkoxy or an alkylcarbonyl, the cycloalkyl, aryl groups optionally including one or more heteroatoms, or R2 and R3 together form an optionally saturated $C_{4-8}$ cyclic group, a $C_{6-10}$ aryl group, the groups being optionally substituted by a halogen, a hydroxy, a $C_{1-5}$ alkoxy, an amino, a sulfino, a sulonfyl, with $R_4$ representing an alkyl, an alkoxy or an alkylcarbonyl, the cyclic and aryl groups optionally including one or more heteroatoms.

21 Claims, No Drawings

OPTICALLY ACTIVE CHIRAL DIPHOSPHINE LIGANDS

RELATED APPLICATION

This is a continuation of International Application No. PCT/FR01/02550, with an international filing date of Aug. 3, 2001, which is based on French Patent Application No. 00/10269, filed Aug. 3, 2000.

FIELD OF THE INVENTION

This invention relates to the use of chiral diphosphines as optically active ligands for the preparation of diphosphino-metal complexes. The invention also pertains to the diphosphino-metal complexes comprising a chiral diphosphine as ligand and the asymmetric catalysis processes employing these complexes. The invention envisages more particularly the use of these diphosphino-metal complexes in asymmetric hydrogenation or isomerization processes for the synthesis of organic products of specified chirality.

BACKGROUND

Known in the prior art are different ligands used for the synthesis of diphosphino-metal complexes having catalytic properties in asymmetric hydrogenation. One can cite, e.g., the compound BINAP described by the Takasago company in European patent applications nos. 444 930 and 295 109, the compound MeOBIPHEP described by the Hoffmann-La Roche company in European patent application no. 398132 and PCT application No. WO 93/15090.

SUMMARY OF THE INVENTION

This invention relates to an (R) or (S) chiral diphosphine of formula (I):

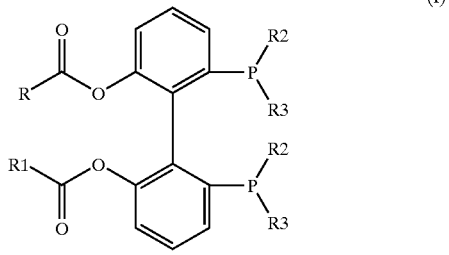

wherein R and R1, which can be identical or different, represent an optionally saturated $C_{1-10}$ alkyl group, an optionally saturated $C_{3-9}$ cycloalkyl group, a $C_{5-10}$ aryl group, the groups being optionally substituted by a halogen, a hydroxy, a $C_{1-5}$ alkoxy, an amino such as $NH_2$, $NHR_4$, $N(R_4)_2$, a sulfino, a sulonfyl, with $R_4$ representing an alkyl, an alkoxy or an alkylcarbonyl, the alkyl, cycloalkyl, aryl groups optionally including one or more heteroatoms or R and R1 together represent an optionally saturated $C_{2-6}$ substituted alkyl group, an optionally saturated $C_{3-9}$ cycloalkyl group, a $C_{5-10}$ aryl group, the cycloalkyl or aryl groups being optionally substituted by a $C_{1-5}$ alkyl, a halogen, a hydroxy, a $C_{1-5}$ alkoxy, an amino, a sulfino, a sulonfyl, with $R_4$ representing an alkyl, an alkoxy or an alkylcarbonyl, the alkyl, cycloalkyl, aryl groups optionally including one or more heteroatoms, R2 and R3, which can be identical or different, represent an optionally saturated $C_{3-8}$ cycloalkyl group, a $C_{6-10}$ aryl group, the groups being optionally substituted by a halogen, a hydroxy, a $C_{1-5}$ alkoxy, an amino, a sulfino, a sulonfyl, with $R_4$ representing an alkyl, an alkoxy or an alkylcarbonyl, the cycloalkyl, aryl groups optionally including one or more heteroatoms, or R2 and R3 together form an optionally saturated $C_{4-8}$ cyclic group, a $C_{6-10}$ aryl group, the groups being carefully substituted by a halogen, a hydroxy, a $C_{1-5}$ alkoxy, an amino, a sulfino, a sulonfyl, with $R_4$ representing an alkyl, an alkoxy or an alkylcarbonyl, the cyclic and aryl groups optionally including one or more heteroatoms.

DETAILED DESCRIPTION

The applicant has developed new diphosphino-metal complexes comprising a chiral diphosphine as optically active ligand particularly useful for the synthesis of organic products of specified chirality with very high yields and enantioselectivity.

Thus, one aspect of the invention is a (R) or (S) chiral diphosphine of formula (I):

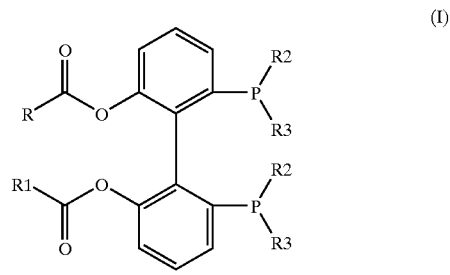

in which:

R and R1, which can be identical or different, represent an optionally saturated $C_{1-10}$ alkyl group, an optionally saturated $C_{3-9}$ cycloalkyl group, a $C_{5-10}$ aryl group, the groups being optionally substituted by a halogen, a hydroxy, a $C_{1-5}$ alkoxy, an amino such as $NH_2$, $NHR_4$, $N(R_4)_2$, a sulfino, a sulonfyl, with $R_4$ represnting an alkyl, an alkoxy or an alkylcarbonyl, the cycloalkyl, aryl groups optionally comprising one or more heteroatoms such as O, N, S, Si, or R and R1 together represent an optionally saturated $C_{2-6}$ substituted alkyl group, an optionally saturated $C_{3-9}$ cycloalkyl group, a $C_{5-10}$ aryl group, the cycloalkyl or aryl groups being optionally substituted by a $C_{1-5}$ alkyl, a halogen, a hydroxy, a $C_{1-5}$ alkoxy, an amino such as $NH_2$, $NHR_4$, $N(R_4)_2$, a sulfino, a sulonfyl, with $R_4$ representing an alkyl, an alkoxy or an alkylcarbonyl, cycloalkyl, aryl groups optionally comprising one or more heteroatoms such as O, N, S, Si, R2 and R3, which can be identical or different, represent an optionally saturated $C_{3-8}$ cycloalkyl group, a $C_{6-10}$ aryl group, the groups being optionally substituted by a halogen, a hydroxy, a $C_{1-5}$ alkoxy, an amino such as $NH_2$, $NHR_4$, $N(R_4)_2$, a sulfino, a sulonfyl, with $R_4$ representing an alkyl, an alkoxy or an alkylcarbonyl, said alkyl, cycloalkyl, aryl groups optionally comprising one or more heteroatoms such as O, N, S, Si, or R2 and R3 together form an optionally saturated $C_{4-8}$ cyclic group, a $C_{6-10}$ aryl group, the groups being optionally substituted by a halogen, an hydroxy, a $C_{1-5}$ alkoxy, an amino such as $NH_2$, $NHR_4$, $N(R_4)_2$, a sulfino, a sulonfyl, with $R_4$ representing an alkyl, an alkoxy or an alkylcarbonyl, the alkyl, cycloalkyl, aryl groups optionally comprising one or more heteroatoms such as O, N, S, Si, as optically active ligand for preparation of a diphosphino-metal complex.

The chiral diphosphines of formula (I) can be used according to the invention for preparation of many types of diphosphino-metal complexes.

A first group of diphosphino-metal complexes prepared using the chiral diphosphines of formula (I) according to the invention corresponds to formula (II) below:

$$M_xH_yX_z(L)_2(Sv)_p \tag{II}$$

in which,
- M represents a metal such as ruthenium, rhodium or iridium;
- X represents a halogen such as chlorine, bromine, fluorine or iodine;
- Sv represents a tertiary amine, a ketone, an ether;
- L represents a (R) or (S) chiral diphosphine of formula (I) above;
- y is a whole number equal to 0 or 1;
- x is a whole number equal to 1 or 2;
- z is a whole number equal to 1 or 4;
- p is a whole number equal to 0 or 1.

Among the diphosphino-metal complexes of formula (II), the invention envisages more particularly the complexes of formulas (IIA) and (IIB).

The complexes of formula (IIA) are those in which y=0, and then x=2, z=4 and p=1. These complexes correspond to formula (IIA) below:

$$M_2X_4L_2(Sv) \tag{IIA}$$

in which M, X, L and Sv have the same meanings as in formula (II).

The following can be cited as examples of complexes of formula (IIA):

- Ru$_4$Cl$_2$((R) or (S) CH$_3$CHOO-Binap)$_2$.N(Et)$_3$, also designated di(2,2'-bis(diphenylphosphino) (R) or (S)-6,6'-diacetoxybiphenyl)-tetrachloro diruthenium triethyl-amine,
- Ru$_4$Cl$_2$((Me)$_2$CHCOO-Binap)$_2$.N(Et)$_3$, also designated di(2,2'-bis(diphenyl-phosphino) (R) or (S)-6,6'-diisobutanoyloxybiphenyl)-tetrachloro diruthenium triethyl-amine,
- Ru$_4$Cl$_2$((CH$_3$)$_3$CCOO-Binap)$_2$.N(Et)$_3$, also designated di(2,2'-bis(diphenylphos-phino) (R) or (S)-6,6'-ditrimethylacetoxybiphenyl)-tetrachloro diruthenium triethyl-amine,
- Ru$_4$Cl$_2$((Me)$_2$CHCH$_2$COO-Binap)$_2$.N(Et)$_3$,
- Ru$_4$Cl$_2$(CH$_3$COO-Binap)$_2$.CO(Me)$_2$,
- Ru$_4$Br$_2$(CH$_3$COO-Binap)$_2$.N(Et)$_3$,
- Ru$_4$Br$_2$((Me)$_2$CHCOO-Binap)$_2$.N(Et)$_3$,
- Ru$_4$Br$_2$((CH$_3$)$_3$CCOO-Binap)$_2$.N(Et)$_3$,
- Ru$_4$Br$_2$((Me)$_2$CHCH$_2$COO-Binap)$_2$.N(Et)$_3$,
- Ru$_4$Br$_2$(CH$_3$COO-Binap)$_2$.CO(Me)$_2$,
- Ru$_4$Br$_2$((Me)$_2$CHCOO-Binap)$_2$.CO(Me)$_2$,
- Ru$_4$Br$_2$((CH$_3$)$_3$CCOO-Binap)$_2$.CO(Me)$_2$,
- Ru$_4$Br$_2$((Me)$_2$CHCH$_3$COO-Binap)$_2$.CO(Me)$_2$,
- Ru$_4$Br$_2$(C$_6$H$_5$COO-Binap)$_2$.CO(Me)$_2$,
- Ru$_4$Br$_2$(C$_6$H$_{11}$COO-Binap)$_2$.CO(Me)$_2$,
- Ru$_4$Br$_2$(C$_4$H$_3$OCOO-Binap)$_2$.CO(Me)$_2$,
- Ru$_4$Br$_2$(CH$_3$OCH$_2$COO-Binap)$_2$.CO(Me)$_2$, The complexes of formula (IIB) are those in which y=1 and then x=1, z=1 and p=0. These complexes correspond to formula (IIB) below:

$$MHXL_2 \tag{IIB}$$

in which M, X and L have the same meanings as in formula (II) and H represents a hydrogen atom.

A second group of diphosphino-metal complexes prepared using the chiral diphosphines of formula (I) according to the invention corresponds to formula (III) below:

$$MX_j(Ar)_mLY_n \tag{III}$$

in which,
- M, X, L have the same meanings as in formula (II);
- Ar represents an olefin such as ethylene, 1,3-butadiene, cyclohexadiene, norbonadiene, cycloocta-1,5-diene, a pi-allyl, a nitrile such as acetonitrile, an arene of formula (IV):

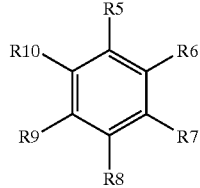

(IV)

in which R5, R6, R7, R8, R9 and R10, which can be identical or different, are selected from among a hydrogen atom, a C$_{1-5}$ alkyl group, an isoalkyl group, a tertioalkyl group, an alkoxy group, the groups comprising one or more heteroatoms such as O, N and Si;
- Y represents an anion, such as ClO$_4^-$, BF$_4^-$, PF$_6^-$;
- j is a whole number equal to 0 or 1;
- m is a whole number equal to 1, 2 or 4;
- n is a whole number equal to 1 or 2.

A third group of diphosphino-metal complexes prepared using the chiral diphosphines of formula (I) according to the invention corresponds to formula (V) below:

$$(MX(P(R_{11})_2(R_{12}))L)_2X \tag{V}$$

in which
- M, X and L have the same definitions as in formula (II), and R$_{11}$ and R$_{12}$, which can be identical or different, represent a phenyl or a phenyl substituted by an alkyl, an alkoxy or a dialkylamino.

A fourth group of diphosphino-metal complexes prepared using the chiral diphosphines of formula (I) according to the invention corresponds to formula (VI) below:

$$M(L)Z_2 \tag{VI}$$

in which,
- M and L have the same meanings as in formula (II) and Z represents an acetate group of formula R$_{13}$COO$^-$, a diacetate group of formula $^-$OOCR$_{13}$COO$^-$, an aminoacetate group of formula R$_{13}$CH(NH$_2$)COO$^-$, in which R13 represents a C$_{1-4}$ alkyl, a C$_{1-4}$ halogenoalkyl, an optionally substituted phenyl.

A fifth group of diphosphino-metal complexes prepared using the chiral diphosphines of formula (I) according to the invention corresponds to formula (VII) below:

$$(M(L)WX_k)_nZ'_p \tag{VII}$$

in which:
- M, L and X have the same meanings as in formula (II);

W represents zinc, aluminum, titanium or tin;

Z' represents:

either an acetate group of formula $R_{14}COO^-$ in which R14 represents a $C_{1-4}$ alkyl, a $C_{1-4}$ halogenoalkyl, an optionally substituted phenyl, and in this case n=1 and p=2, and when W is Zn then k=2, when W is Al then k=3, and when W is Ti or Sn then k=4, or a tertiary amine, such as triethylamine, and in this case n=2 and p=1, and when W is Zn then k=4, when W is Al then k=5, and when W is Ti or Sn then k=6.

A sixth group of diphosphino-metal complexes prepared using the chiral diphosphines of formula (I) according to the invention corresponds to formula (VIII) below:

$$MH(L)_2Y \qquad (VIII)$$

in which H represents a hydrogen atom, M and L have the same meanings as in formula (II);

Y represents an anion such as $ClO_4^-$, $BF_4^-$, $PF_6^-$.

A seventh group of diphosphino-metal complexes prepared using the chiral diphosphines of formula (I) according to the invention corresponds to formula (IX) below:

$$M(L)Y_2 \qquad (IX)$$

in which M and L have the same meanings as in formula (II) and Y represents an anion such as $ClO_4^-$, $BF_4^-$, $PF_6^-$.

An eighth group of diphosphino-metal complexes prepared using the chiral diphosphines of formula (I) according to the invention corresponds to formula (X) below:

$$M(L)_2Y \qquad (X)$$

in which M and L have the same meanings as in formula (II) and Y represents an anion such as $ClO_4^-$, $BF_4^-$, $PF_6^-$.

The (R) or (S) chiral diphosphines (I) can be prepared by processes well known in the art from compounds of formula (XI):

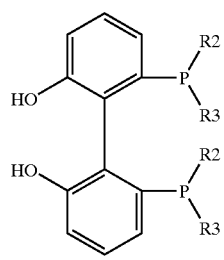

(XI)

in which R2 and R3 have the same meanings as in formula (I).

These processes consist of bringing together a compound of formula (XI) and a compound derived from an acid halide of formula RCOX or R1COX, in which R and R1 have the same meanings as in formula (I) and X has the same meaning has in formula (II).

The compound of formula (XI) is prepared according to the process described in PCT patent application No. WO 93/15090 from the compound of formula (XII):

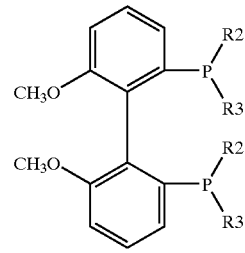

(XII)

in which R2 and R3 have the same meanings as in formula (I).

The complexes of formulas (II), (III) and (V) can be prepared by analogy according to methods described in the prior art.

Thus, according to the process described in European patent application no. 174 057, the complexes of formula (II) can be prepared from a compound of formula (XIII):

$$MX_2(COD)_2 \qquad (XIII)$$

in which M and X have the same meanings as in formula (II) and COD represents cyclooctadiene.

Similarly, according to the process described in European patent application no. 366,390, the complexes of formula (III) can be prepared from a compound of formula (XIV):

$$(MX_2(Ar))_2 \qquad (XIV)$$

in which M, X and Ar have the same meanings as in formula (III).

Finally, according to the process described in European patent application no. 470 756, the compounds of formula (V) can be prepared from a compound of formula (XV):

$$(MX(P(R11)_2(R12))(DMA))_2X \qquad (XV)$$

in which M, X, R11 and R12 have the same definitions as in formula (V) and DMA represents dimethylacetamide.

The complexes of formulas (VI), (VII), (VIII), (IX) and (X) can be prepared by analogy according to methods described in the prior art.

Thus, the complexes of formulas (VI and (VII) can be obtained from compounds of formula (IIA) by analogy by the processes described in European patent applications nos. 245 960 and 271 310. The complexes of formulas (VIII), (IX) and (X) can be obtained from compounds of formula (IIB) by analogy by the processes described in European patent applications nos. 256 634, 245 959 and 271 310.

The invention also pertains to the diphosphino-metal complexes of formulas (II), (III), (V), (VI), (VII), (VIII), (IX) and (X) as well as their use as a catalyst in asymmetric catalysis processes. The invention envisages more particularly their use in asymmetric hydrogenation or asymmetric isomerization processes.

The invention pertains more specifically to their use in a process for asymmetric hydrogenation of unsaturated compounds carrying functional groups of formula (XVI) below:

(XVI)

in which:

A and B are different and selected from among a $C_{1-5}$ alkyl group, an aryl group, a $C_{1-7}$ hydroxycarbonyl group, a $C_{1-7}$ alkoxycarbonyl group, a $C_{1-10}$ aryloxycarbonyl group, a $C_{1-7}$ halogenoalkyl group, a heteroaryl group, an optionally saturated cycloalkyl group, the alkyl, aryl, cycloalkyl groups optionally comprising one or more substituents selected from among a halogen such as chlorine, fluorine, bromine, an —$NO_2$ group, a $C_{1-5}$ alkyl, a $C_{1-5}$ alkoxy, an optionally fused $C_{1-7}$ cycloalkyl, an optionally fused aryl group, possibly substituted by a halogen, a $C_{1-5}$ alkyl, a $C_{1-5}$ alkoxy, the alkyl, cycloalkyl, aryl groups optionally comprising one or more heteroatoms such as O, N or Si.

A and B together can also form a $C_{2-6}$ substituted alkyl group, an optionally saturated $C_{3-9}$ cycloalkyl group, a $C_{5-10}$ aryl group, the groups optionally being substituted by a $C_{1-5}$ alkyl, a halogen, a hydroxy, a $C_{1-5}$ alkoxy, an amino such as $NH_2$, $NHR_4$, $N(R_4)_2$, a sulfino, a sulfonyl, in which $R_4$ represents an alkyl, an alkoxy or an alkylcarbonyl, the alkyl, cycloalkyl, aryl groups optionally comprising one or more heteroatoms such as O, N, S, Si;

Q represents an oxygen, an —NR16, —NOR16 or —$C(R16)_2$ group, in which R16 is selected from among a $C_{1-5}$ alkyl, an aryl group and a heteroaryl group substituted by a $C_{1-4}$ alkyl.

Among the compounds of formula (XVI), one can cite as nonlimitative examples the following compounds: the ene-acid or ester derivatives, the ene-alcohol or ether derivatives, the ene-amide derivatives, the ene-amino derivatives, the beta-ketoacid or ester derivatives, the gamma-ketoacid or ester derivatives, the beta, gamma-diketoacid or ester derivatives, the alpha-amid-beta-ketoacid or ester derivatives, the halogeno-ketone derivatives, the hydroxy or alkoxy-ketone derivatives, the imine derivatives.

A preferred asymmetric hydrogenation process according to the invention comprises the treatment of a compound of formula (XVI), in a suitable solvent, in the presence of a catalytic complex of formula (II), (III), (V), (VI), (VII), (VII), (IX) or (X) as catalyst under the following preferred operating conditions:

A temperature between 0 and +150° C.

A hydrogen pressure between 1 and 20 bar or between 1 and 100 bar.

An amount of catalyst in relation to the amount of substrate comprised between 1/50,000 and 1/10, preferably between 10/10,000 and 1/10, and most preferably between 10/100 and 1/10.

The duration of hydrogenation will generally be equal to or greater than 1 hour. As a function of the substrate and the catalyst, it could be between 1 hour and 70 hours.

Any solvent can be used in isolation or mixture such that it will dissolve the substrate and not affect the reaction. Among the solvents that can be used in the above process, one can cite water, a hydrocarbon such as hexane, heptane, octane, nonane, decane, benzene, toluene and xylene, an ether such as tetrahydrofuran, tetrahydropyran, dioxane, dimethoxyethane, diisopropyl ether and diethylene glycol dimethyl ether, an ester such as a formate or an alkyl acetate such as ethyl formate, ethyl acetate, butyl acetate and ethyl propionate, a ketone such as acetone, diethyl ketone, diisopropyl ketone, methylisobutyl ketone, methylethyl ketone and acetylacetone, an alcohol such as methanol, ethanol, n-propanol and iso-propanol, a nitrile such as acetonitrile, an alkyl halide such as dichloromethane, chloroform and 1,2-dichloroethane, an amine such as dimethylamine, triethylamine, diisobutyl amine, triethylamine, N-methyl piperidine, ethyl diisopropyl amine, N-methylcyclohexyl amine and pyridine, an organic acid such as acetic acid, propionic acid and formic acid, an amide such as dimethyl formamide and N-methyl formamide.

When implementing the reaction, it is recommended to use the substrate at a concentration in the solvent of 0.1 to 2 moles/liter.

Other advantages and characteristics of the invention will become apparent from the examples below which are presented on a nonlimitative basis.

I—Preparation of the Ligands

EXAMPLE 1

Preparation of the Ligand (R)-HOBIPHEP: (R)-6,6'-dihydroxybiphenyl-2,2'-diyl bis(diphenyl phosphine)

The process described in the PCT patent application no. WO 93/15090 was applied.

The compound (R)-HOBIPHEP was obtained with a quantitative yield.

EXAMPLE 2

Preparation of the Ligand (R)—$CH_3$COOBIPHEP (Summary A): (R)-6,6'-acetoxybiphenyl-2,2'-diyl bis(diphenyl phosphine)

Under nitrogen in a 250-ml four neck flask, (R)-HOBIPHEP (5.65 g; $1.01 \cdot 10^{-2}$ mol) was suspended in 100 ml of DMF. $K_2CO_3$ (7 g) was added at 20/24° C. After 10 minutes of agitation, acetyl chloride (1.7 g; $2.14 \cdot 10^{-2}$ mol) was added drop by drop. This was maintained at a temperature of 24/25° C. for 48 hours.

The reaction medium was concentrated. The residue was taken up with a solution of 220 ml of ethyl acetate and 50 ml of water.

After decantation, the organic phase was washed with a solution of sodium chloride (3 times 30 ml). The organic phase was dried, filtered then concentrated under vacuum.

This produced 4.5 g of product in the form of clear maroon crystals.

The product was purified by column chromatography. Eluent: $CH_2Cl_2$/hexane (½).

This yielded 3.35 g of product in the form of white crystals.

Yield: 59% of purified product.

$(\alpha)_D^{23}$:+52.4°

$^1H$ NMR spectrum: 7.4–7.05 ppm (m, 26H, H arom.); 1.7 ppm (S, 6H, $CH_3CO$).

$^{13}C$ NMR spectrum: 168.9 (CO); 122.8–148.9 (C arom.); 20.5 (C methyl).

EXAMPLE 3

Preparation of the Ligand (R)—$(CH_3)_2$CHCOOBIPHEP (Summary B): (R)-6,6'-isobutanoyloxy biphenyl-2,2'-diyl bis(diphenyl phosphine)

In a 250-ml four neck flask under agitation, (R)-HOBIPHEP (4 g; $7.21 \cdot 10^{-3}$ mol) was suspended in 72 ml of THF. The medium was cooled to −20° C. and NaH (0.61 g; 0.025 mol) was added. The medium was left under agitation at −20° C. for 1 hour. The medium was cooled to −30° C. and then 98% isobutyric acid chloride (1.6 ml; 0.025 ml) was added drop by drop. The medium was allowed to heat up to room temperature, i.e., 20° C. (at the end of 1 hour). The medium was hydrolyzed with 50 ml of water. The reaction was exothermal. Extraction was performed with 40 ml of ethyl acetate. The organic phase was washed with water (20 ml) then with an aqueous solution of sodium chloride (2 times 20 ml). The organic phase was dried, filtered and then concentrated under vacuum.

5.6 g of product was obtained in the form of a maroon gum.

The product was purified by column chromatography. Eluent: $CH_2Cl_2$/hexane (½).

2.3 g of product was obtained in the form of white crystals.

Yield: 31.4% of purified product.

$(\alpha)_D^{23}=:+49.6°$ $^1H$ NMR spectrum: 7.2–7.55 ppm (m, 26H, H arom.); 2.2–2.35 ppm (m, 2H, —CH—), 0.8–1.05 ppm (m, 12H, $(CH_3)_2$—).

$^{13}C$ NMR spectrum: 175 (CO); 123–149 (C arom.); 34 (CH—); 19 (C methyl).

EXAMPLE 4

Preparation of the Ligand (R)—(CH$_3$)$_3$CCOOBIPHEP (Summary C): (R)-6,6'-tertiobutanoyloxybiphenyl-2,2'-diyl bis(diphenyl phosphine)

Employing the same procedure as example 2.

Yield: 58%.

$^1H$ NMR spectrum: 7.05–7.4 ppm (m, 26 H, H arom.); 0.8 ppm (m, 18H, (CH$_3$)).

$^{13}C$ NMR spectrum: 176 (CO); 122.8–149 (C arom.); 39.5 (C); 28 (C methyl).

EXAMPLE 5

Preparation of the Ligand (R)—(CH$_3$)$_2$CHCH$_2$COOBIPHEP (Summary D): (R)-6,6'-isovaleroyloxybiphenyl-2,2'-diyl bis(diphenyl phosphine)

Employing the same operating mode as example 3.

The reaction medium was left for 24 hours at 20° C. before hydrolysis.

5.1 g of product was obtained in the form of an oil.

Purification was performed by column chromatography. Eluent: $CH_2Cl_2$/hexane (½).

1.7 g of product was obtained in the form of white crystals.

Yield: 37% of purified product.

$^1H$ NMR spectrum: 7.2–7.55 ppm (m, 26H, H arom.); 1.85–2.05 ppm (m, 6H, CH$_2$CH—), 0.95 ppm (d, 12H, (CH$_3$)2—).

$^{13}C$ NMR spectrum: 171 (CO); 123–149.4 (C arom.); 43.1 (CH—); 25.6 (CH$_3$); 22.7 (C methyl).

EXAMPLE 6

Preparation of the Ligand (R)—C$_6$H$_5$COOBIPHEP (Summary E): (R)-6,6'-benzoyloxybiphenyl-2,2'-diyl bis(diphenyl phosphine)

In a 500-ml four neck flask NaH (2.6 g; 0.108 mol) was added to THF (64 ml).

(R)-HOBIPHEP (0.0257 mol) was added at 20° C. in solution in DMF (64 ml) for 45 minutes. It was left under agitation at 20° C. for 1 hour. The medium was then cooled to −40° C. Benzoyl chloride (8.18 ml, source: Fluka) was introduced drop by drop for 20 minutes. The medium was maintained at −40/45° C. for 45 minutes.

A 10% solution of hydrochloric acid (75 ml) was added.

The temperature was allowed to climb to 0° C. during the addition.

Upon termination of the hydrolysis, the temperature was brought to room temperature. The medium was extracted with ethyl acetate (50 ml and 40 ml). The organic phase was washed with water (2 times 20 ml). The organic phase was dried, filtered and then concentrated under vacuum.

The anticipated product was obtained in the form of a maroon oil.

Purification was performed by column chromatography. Eluent: hexane then toluene.

The product was obtained in the form of white crystals.

Yield: 55.2% of purified product.

$^1H$ NMR spectrum: 7–7.55 ppm (m, H arom.).

$^{13}C$ NMR spectrum: 164 (CO); 123–149 (C arom.).

EXAMPLE 7

Preparation of the Ligand (R)—C$_6$H$_{11}$COOBIPHEP (Summary 7): (R)-6,6'-cyclohexanoylbiphenyl-2,2'-diyl bis(diphenyl phosphine)

Following the same procedure as that of example 6 but without purification by column chromatography.

The product was obtained in the form of white crystals.

Yield: 52.5% of product.

$^1H$ NMR spectrum: 7.15–7.5 ppm (m, 26H, H arom.); 1.9 ppm (m, 2H, —CH—), 1–1.6 ppm (m, 20H, —(CH$_2$)—).

$^{13}C$ NMR spectrum: 172 (CO); 123–149.5 (C arom.); 43 (CH—); 26 and 28 ppm (CH$_2$).

EXAMPLE 8

Preparation of the Ligand (R)—(C$_4$H$_3$O)COOBIPHEP (Summary G): (R)-6,6'-2-furanoyloxybiphenyl-2,2'-diyl bis(diphenyl phosphine)

Following the same procedure as that of example 6 with purification by column chromatography. Eluent: $CH_2Cl_2$.

The product was obtained in the form of white or pale yellow crystals.

Yield: 84.2% of purified product.

$^1H$ NMR spectrum: 7.6–6.35 ppm (m, H arom.+H furyl).

$^{13}C$ NMR spectrum: 156 (CO); 110–149 (C arom.).

EXAMPLE 9

Preparation of the Ligand (R)—CH$_3$OCH$_2$COOBIPHEP (Summary H): (R)-6,6'-methoxyacetyloxybiphenyl-2,2'-diyl bis(diphenyl phosphine)

Following the same procedure as that of example 6 without purification by column chromatography.

The product was obtained in the form of white or pale yellow crystals.

Yield: 34.8% of product.

$^1H$ NMR spectrum: 7.4–7.08 ppm (m, 26H, H arom.); 3.6 ppm (s, 4H, —OCH$_2$O—), 3.25 ppm (s, 6H, CH$_3$O—).

$^{13}$NMR spectrum: 169 (CO); 123–149 (C arom.); 69 (CH$_2$O—); 60 (C methoxy).

II-Preparation of catalysts

| Exp. no. | Formula R = R1 | Summary | Name |
|---|---|---|---|
| 10 | $CH_3CO_2$ | (R)-cA1 | (R)-acetyloxyBIPHEPRuBr$_2$ acetone |
| 11 | $CH_3CO_2$ | (R)-cA | (R)-acetyloxyBIPHEPRu(OAC)$_2$ |
| 12 | $(CH_3)_2CHCO_2$ | (R)-cB | (R)-iso-propanoyloxyBIPHEPRu(OAC)$_2$ |
| 13 | $(CH_3)_2CHCO_2$ | (R)-cB | (R)-iso-propanoyloxyBIPHEPRuBr$_2$ |
| 14 | $(CH_3)_3CCO_2$ | (R)-cC | tertio-butanoyloxyBIPHEPRuBr$_2$ |
| 15 | $(CH_3)_2CHCH_2CO_2$ | (R)-cD | iso-valeroyloxyBIPHEPRuBr$_2$ |
| 16 | $C_6H_5CO_2$ | (R)-cE | benzoyloxyBIPHEPRuBr$_2$ |
| 17 | $C_6H_{11}CO_2$ | (R)-cF | cyclohexanoyloxyBIPHEPRuBr$_2$ |
| 18 | $C_4H_3OCO_2$ | (R)-cG | 2-furanoyloxyBIPHEPRuBr$_2$ |
| 19 | $CH_3OCH_2CO_2$ | (R)-cH | methoxyacetyloxyBIPHEPRuBr$_2$ |

EXAMPLE 10

Preparation of the Catalyst: the Complex (RuBr$_2$(R)—CH$_3$COOBIPHEP))$_2$.acetone The following were introduced into a hydrogenation chamber: the ligand (R)—CH$_3$COOBIPHEP (20.8 mg; 0.032 mol) and 1.5-bis methylallylcyclooctadiene ruthenium (8.4 mg; 0.026 mol) in 1.5 ml of acetone. Hydrobromic acid in solution in methanol (0.0128 ml of a 0.5 M solution) was then added via syringe. This was left for 15 minutes at 20° C. under agitation.

This produced a catalytic solution of the complex (RuBr$_2$(R)—CH$_3$COOBIPHEP))$_2$.acetone.

EXAMPLE 11

Preparation of the Catalyst: the Complex Ru(R)—CH$_3$COOBIPHEP)(OAc)$_2$

The following was introduced into a 100-ml three neck flask under nitrogen: the ligand (R)—CH$_3$COOBIPHEP (8 g) in toluene (50 ml).

Sodium acetate (4.48 g) and ruthenium cyclooctadiene dichloride (CODRuCl2) (3.85 g) were added.

Acetic acid (15.5 g) was added quickly. Heated at reflux (93° C.) for 22 hours.

Cooled to 65° C. Distilled under vacuum the azeotrope acetic acid/toluene. Repeated addition of toluene (40 ml) to bring the acetic acid to a residual volume of 20 ml.

Cooled to 50° C. and acetone was introduced (112 ml). It was allowed to cool to 20° C. and agitated for 1 hour.

Filtered and the filtrate was concentrated. The residue was taken up with toluene then concentrated (2 times 20 ml).

At 70° C. drop by drop addition under agitation of heptane (52 ml) (duration of the addition 52 minutes).

Allowed to cool to 20° C.

Filtered and rinsed with heptane (2 times 20 ml). Dried under bell.

This produced dark green crystals.

Yield: 30.2%.

Elemental analysis: 58.6% C; 4.6% H.

EXAMPLE 12

Preparation of the Catalyst: the Complex Ru(r)—(CH$_3$)$_2$CHCOOBIPHEP)(OAc)$_2$ The same procedure as in example 11 was followed. Dark green crystals were obtained.

Yield: 83%.

Examples 13 to 19 followed the same procedure as in example 10.

III—Application in Asymmetric Hydrogenation

EXAMPLE 20

Asymmetric Hydrogenation of Ethylbenzoylacetate
Ligand of the Catalyst: A

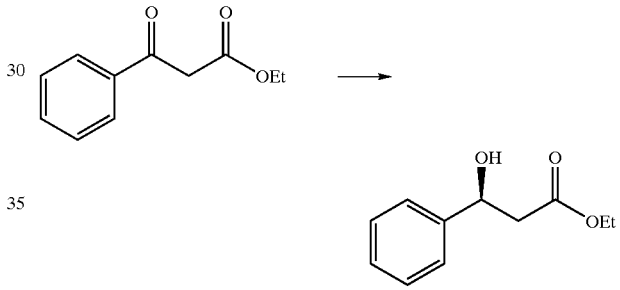

To the catalytic solution of example 10 were added ethyl benzoylacetate (0.5 g; 0.0026 mol) and 5 ml of ethanol. This was placed under a pressure of 20 bar of hydrogen. The medium was heated to 50° C. and left for 22 hours under agitation.

The medium was concentrated.

This produced 0.54 g of product in the form of a brown liquid.

Yield: Chemical purity: 82%.

Enantiomer excess: 97.8%

EXAMPLES 21 TO 23

Same Operating Procedure as that of Example 20 with Ligands B, C or D

| Example | L*ligand | Catalyst | Operating conditions | Yield | Enantiomer excess |
|---|---|---|---|---|---|
| 21 | B | (RuL*Br$_2$) | Substrate/catalyst = 100 | | 95.7 |
| 22 | D | (RuL*Br$_2$) | idem | | 95.8 |
| 23 | C | (RuL*Br$_2$) | idem | | 96.2 |

EXAMPLE 24

Asymmetric Hydrogenation of the Hydroxyacetone Compound Ligand A

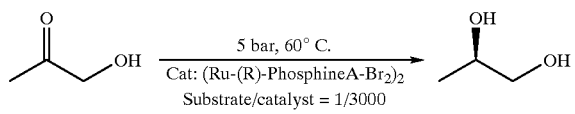

5 bar, 60° C.
Cat: (Ru-(R)-PhosphineA-Br$_2$)$_2$
Substrate/catalyst = 1/3000

The same procedure as in example 20 was performed employing the indicated hydrogen pressure, temperature and substrate/catalyst ratio (S/C) in the reaction.

The anticipated product was obtained in the form of a brown liquid.

Yield: Chemical purity: 72.7%

Enantiomer excess: 96.1%

EXAMPLES 25 TO 33

Same Operating Procedure as in Example 24 with the Ligands B, C, D, E, F, G or H Catalyst (RuL*Br$_2$)

| Example | L*ligand | Substrate/catalyst | Yield | Enantiomer excess |
|---|---|---|---|---|
| 25 | B | 1/3000 | Quantitative | 95.7 |
| 26 | D | 1/3000 | Idem | 95.8 |
| 27 | C | 1/3000 | Idem | 96.2 |
| 28 | A | 1/1000 | Idem | 95.5 |
| 29 | C | 1/1000 | Idem | 96.1 |
| 30 | E | 1/1000 | Idem | 96.6 |
| 31 | F | 1/1000 | Idem | 96.5 |
| 32 | G | 1/1000 | Idem | 95.5 |
| 33 | H | 1/1000 | Idem | 96.6 |

EXAMPLE 34

Asymmetric Hydrogenation of the Hydroxyacetone Compound

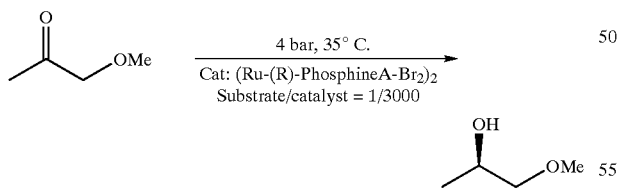

4 bar, 35° C.
Cat: (Ru-(R)-PhosphineA-Br$_2$)$_2$
Substrate/catalyst = 1/3000

The same procedure as in example 20 was performed employing the indicated hydrogen pressure, temperature and substrate/catalyst ratio (S/C) in the reaction.

The anticipated product was obtained in the form of a brown liquid.

Yield: 80–95%

Enantiomer excess: 97%

EXAMPLES 35 TO 39

Same Operating Procedure as in Example 34 with the Ligands B, C, D, E, F, G or H Catalyst (RuL*Br$_2$)

| Example | L*ligand | Yield | Enantiomer excess |
|---|---|---|---|
| 35 | C | 80–95% | 97.2 |
| 36 | E | Idem | 97.6 |
| 37 | F | Idem | 97.2 |
| 38 | G | Idem | 97.9 |
| 39 | H | Idem | 97.5 |

EXAMPLE 40

Asymmetric Hydrogenation of the 4-chloroacetoacetate Compound

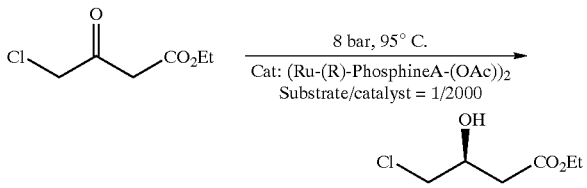

8 bar, 95° C.
Cat: (Ru-(R)-PhosphineA-(OAc))$_2$
Substrate/catalyst = 1/2000

The same procedure as in example 20 was performed employing the indicated hydrogen pressure, temperature and substrate/catalyst ratio (S/C) in the reaction.

The anticipated product was obtained in the form of an oil.

Yield: quantitative.

Chemical purity: 52%.

Enantiomer excess: 94%.

EXAMPLE 41

Same Operating Procedure as in Example 40 with Ligand B Catalyst (RuL*Br$_2$)

| Example | L*ligand | Catalyst | Substrate/catalyst | Yield | Enantiomer excess |
|---|---|---|---|---|---|
| 41* | B | (RuL*Br$_2$) | 1/4000 | Quantitative | 98.4 |

*temperature condition: 75° C.

EXAMPLE 42

Asymmetric Hydrogenation of the N-(1-(2-naphthalenyl)ethenyl) acetamide Compound Ligand A

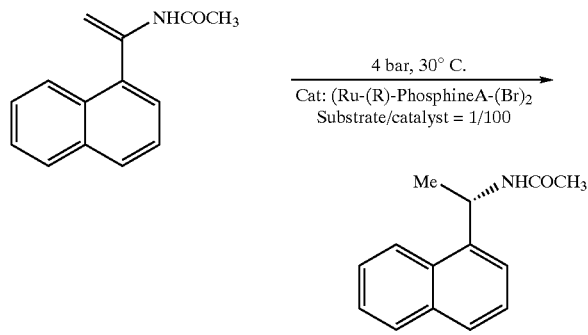

The same procedure as in example 20 was performed employing the indicated hydrogen pressure, temperature and substrate/catalyst ratio (S/C) in the reaction.

The anticipated product was obtained in the form of an orange oil.

Yield: 80–90.

Enantiomer excess: 85.8%.

EXAMPLES 43 TO 47

Same Operating Procedure as in Example 42 with the Ligands B, C, E, F, and G. Catalyst (RuL*Br$_2$)

| Example | L*ligand | Yield | Enantiomer excess |
|---|---|---|---|
| 43 | B | 80–90% | 87.5% |
| 44 | C | Idem | 91.2% |
| 45 | E | Idem | 90.8% |
| 46 | F | Idem | 88.7% |
| 47 | G | Idem | 89.7% |

EXAMPLE 48

Asymmetric Hydrogenation of the Dimethyl Itaconate Compound Ligand A

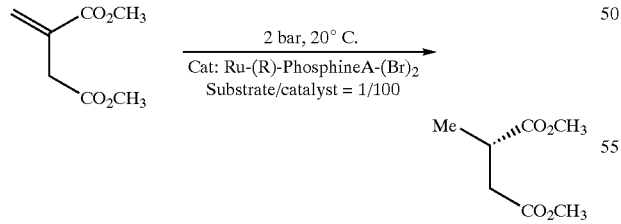

The same procedure as in example 20 was performed employing the indicated hydrogen pressure, temperature and substrate/catalyst ratio (S/C) in the reaction.

The anticipated product was obtained in the form of a brown liquid.

Yield: 80–90%.

Enantiomer excess: 97.4%.

EXAMPLES 49 TO 53

Same Operating Procedure as in Example 48 with the Ligands C, E, F, G and H Catalyst (RuL*Br$_2$)

| Example | L*ligand | Yield | Enantiomer excess |
|---|---|---|---|
| 49 | C | 80–90% | 97.6% |
| 50 | E | Idem | 96.4% |
| 51 | F | Idem | 97.7% |
| 52 | G | Idem | 93.2% |
| 53 | H | Idem | 97.3% |

What is claimed is:

1. An (R) or (S) chiral diphosphine of formula (I):

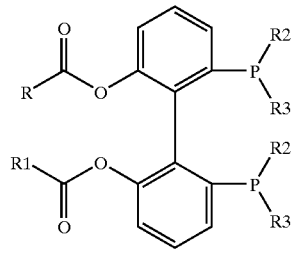

(I)

wherein

R and R1, which can be identical or different, represent an optionally saturated $C_{1-10}$ alkyl group, an optionally saturated $C_{3-9}$ cycloalkyl group, a $C_{5-10}$ aryl group, the groups being optionally substituted by a halogen, an hydroxy, a $C_{1-5}$ alkoxy, an amino, a sulfino, a sulonfyl, with $R_4$ representing an alkyl, an alkoxy or an alkylcarbonyl, the alkyl, cycloalkyl, aryl groups optionally comprising one or more heteroatoms, or R and R1 together represent an optionally saturated $C_{2-6}$ substituted alkyl group, an optionally saturated $C_{3-9}$ cycloalkyl group, a $C_{5-10}$ aryl group, the cycloalkyl or aryl groups being optionally substituted by a $C_{1-5}$ alkyl, a halogen, a hydroxy, a $C_{1-5}$ alkoxy, an amino, a sulfino, a sulonfyl, with $R_4$ representing an alkyl, an alkoxy or an alkylcarbonyl, the alkyl, cycloalkyl, aryl groups optionally comprising one or more heteroatoms, R2 and R3, which can be identical or different, represent an optionally saturated $C_{3-8}$ cycloalkyl group, a $C_{6-10}$ aryl group, the groups being optionally substituted by a halogen, an hydroxy, a $C_{1-5}$ alkoxy, an amino, a sulfino, a sulonfyl, with $R_4$ representing an alkyl, an alkoxy or an alkylcarbonyl, the cycloalkyl, aryl groups optionally comprising one or more heteroatoms, or R2 and R3 together form an optionally saturated $C_{4-8}$ cyclic group, a $C_{6-10}$ aryl group, the groups being optionally substituted by a halogen, a hydroxy, a $C_{1-5}$ alkoxy, an amino, a sulfino, a sulonfyl, with $R_4$ representing an alkyl, an alkoxy or an alkylcarbonyl, the cyclic and aryl groups optionally comprising one or more heteroatoms.

2. A diphosphino-metal complex corresponding to formula (II) below:

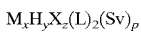

(II)

wherein

M represents a metal;

X represents a halogen;

Sv represents a tertiary amine, a ketone or an ether;

L represents the (R) or (S) chiral diphosphine of formula (I) according to claim 1;

y is a whole number equal to 0 or 1;

x is a whole number equal to 1 or 2;

z is a whole number equal to 1 or 4; and p is a whole number equal to 0 or 1.

3. The diphosphino-metal complex according to claim 2 corresponding to formula (IIA):

$$M_2X_4L_2(Sv) \tag{IIA}$$

in which M, X, L and Sv have the same meanings as in formula (II).

4. The diphosphino-metal complex according to claim 2, selected from the group consisting of:

Ru$_4$Cl$_2$[(R) or (S) CH$_3$CHOO-Binap]$_2$.N(Et)$_3$, also designated di[2,2'-bis(diphenylphosphino) (R) or (S)-6,6'-diacetoxybiphenyl]-tetrachloro diruthenium triethylamine, Ru$_4$Cl$_2$((Me)$_2$CHCOO-Binap)$_2$.N(Et$_3$), also designated di[2,2'-bis(diphenylphosphino) (R) or (S)-6,6'-di-isobutanoyloxybiphenyl]-tetrachloro diruthenium triethylamine, Ru$_4$Cl$_2$((CH$_3$)$_3$CCOO-Binap)$_2$.N(Et)$_3$, also designated di[2,2'-bis(diphenylphosphino) (R) or (S)-6,6'-ditrimethylacetoxybiphenyl]-tetrachloro diruthenium triethylamine, Ru$_4$Cl$_2$((Me)$_2$CHCH$_2$COO-Binap)$_2$.N(Et)$_3$, Ru$_4$Cl$_2$(CH$_3$COO-Binap)$_2$.CO(Me)$_2$, Ru$_4$Br$_2$(CH$_3$COO-Binap)$_2$.N(Et)$_3$, Ru$_4$Br$_2$((Me)$_2$CHCOO-Binap)$_2$.N(Et)$_3$, RU$_4$Br$_2$((CH$_3$)$_3$CCOO-Binap)$_2$.N(Et)$_3$, Ru$_4$Br$_2$((Me)$_2$CHCH$_2$COO-Binap)$_2$.N(Et)$_3$, Ru$_4$Br$_2$(CH$_3$COO-Binap)$_2$.CO(Me)$_2$, Ru$_4$Br$_2$((Me)$_2$CHCOO-Binap)$_2$.CO(Me)$_2$, Ru$_4$Br$_2$((CH$_3$)$_3$CCOO-Binap)$_2$.CO(Me)$_2$, Ru$_4$Br$_2$((Me)$_2$CHCH$_3$COO-Binap)$_2$.CO(Me)$_2$, Ru$_4$Br$_2$(C$_6$H$_5$COO-Binap)$_2$.CO(Me)$_2$, Ru$_4$Br$_2$(C$_6$H$_{11}$COO-Binap)$_2$.CO(Me)$_2$, Ru$_4$Br$_2$(C$_4$H$_3$OCOO-Binap)$_2$.CO(Me)$_2$, and Ru$_4$Br$_2$(CH$_3$OCH$_2$COO-Binap)$_2$.CO(Me)$_2$.

5. The diphosphino-metal complex according to claim 2, corresponding to formula (IIB):

$$MHXL_2 \tag{IIB}$$

wherein M, X and L have the same meanings as in formula (II) and H represents a hydrogen atom.

6. A diphosphino-metal complex corresponding to formula (III) below:

$$MX_j(Ar)_mLY_n \tag{III}$$

wherein

M is a metal, X is a halogen, L is the (R) or (S) chiral diphosphine of formula (I) according to claim 1;

Ar represents an olefin selected from the group consisting of ethylene, 1,3-butadiene, cyclohexadiene, norbornadiene, cycloocta-1,5-diene, a pi-allyl, a nitrile and an arene of formula (IV):

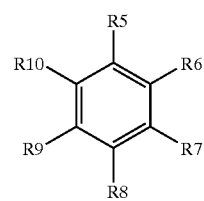

(IV)

wherein R5, R6, R7, R8, R9 and R10, which can be identical or different, are selected from a hydrogen atom, a C$_{1-5}$ alkyl group, an isoalkyl group, a tertioalkyl group and an alkoxy group, the groups comprising one or more heteroatoms;

Y represents an anion;

j is a whole number equal to 0 or 1;

m is a whole number equal to 1, 2 or 4; and n is a whole number equal to 1 or 2.

7. A diphosphino-metal complex corresponding to formula (V):

$$(MX(P(R_{11})_2(R_{12}))L)_2X \tag{V}$$

wherein

M is a metal, X is a halogen and L is the (R) or (S) chiral diphosphine of formula (I) according to claim 1, and R$_{11}$ and R$_{12}$, which can be identical or different, represent a phenyl or a phenyl substituted by an alkyl, an alkoxy or a dialkylamino.

8. A diphosphino-metal complex corresponding to formula (VI):

$$M(L)Z_2 \tag{VI}$$

wherein

M is a metal and L is the (R) or (S) chiral diphosphine of formula (I) according to claim 1, and Z represents an acetate group of formula R$_{13}$COO$^-$, a diacetate group of formula $^-$OOCR$_{13}$COO$^-$, an aminoacetate group of formula R$_{13}$CH(NH$_2$)COO$^-$, in which R13 represents a C$_{1-4}$ alkyl, a C$_{1-4}$ halogenoalkyl, an optionally substituted phenyl.

9. A diphosphino-metal complex corresponding to formula (VII) below:

$$(M(L)WX_k)_nZ'_p \tag{VII}$$

wherein

M is a metal, L is the (R) or (S) chiral diphosphine of formula (I) according to claim 1 and X is a halogen;

W represents zinc, aluminum, titanium or tin;

Z' represents;

either an acetate group of formula R$_{14}$COO$^-$ in which R14 represents a C$_{1-4}$ alkyl, a C$_{1-4}$ halogenoalkyl, an optionally substituted phenyl, and n=1 and p=2, and when W is Zn then k=2, when W is Al then k=3, and when W is Ti or Sn then k=4, or a tertiary amine and n=2 and p=1, and when W is Zn then k=4, when W is Al then k=5, and when W is Ti or Sn then k=6.

10. A diphosphino-metal complex corresponding to formula (VIII):

$$MH(L)_2Y \tag{VIII}$$

wherein H represents a hydrogen atom, M is a metal and L is the (R) or (S) chiral diphosphine of formula (I) according to claim 1; and Y represents an anion.

11. A diphosphino-metal complex according to claim 2, corresponding to formula (IX):

$$M(L)Y_2 \quad (IX)$$

wherein M is a metal and L is a (R) or (S) chiral diphosphine of formula (I) and Y represents an anion.

12. The diphosphino-metal complex according to claim 2, corresponding to formula (X):

$$M(L)_2Y \quad (X)$$

wherein M is a metal and L is a ( R) or (S) chiral diphosphine of formula (I) and Y represents an anion.

13. The chiral diphosphine or diphosphino-metal complex according to one of claims 1 to 12, wherein the heteroatoms are O, N, S or Si;

the amino groups are $NH_2$, $NHR_4$ or $N(R_4)_2$;

M is ruthenium, rhodium or iridium; and

X is chlorine, bromine, fluorine or iodine.

14. A catalyst for an asymmetric catalysis process comprising a diphosphino-metal complex according to claim 2.

15. The catalyst according to claim 14, wherein the asymmetric catalysis process is an asymmetric isomerization process.

16. The catalyst according to claim 14, wherein the asymmetric catalysis process is an asymmetric hydrogenation process.

17. A catalyst comprising a diphosphino-metal complex according to claim 2 and having functional groups of formula (XVI):

(XVI)

wherein

A and B are different and selected from among a $C_{1-5}$ alkyl group, an aryl group, a $C_{1-7}$ hydroxycarbonyl group, a $C_{1-7}$ alkoxycarbonyl group, a $C_{1-10}$ aryloxycarbonyl group, a $C_{1-7}$ halogenoalkyl group, a heteroaryl group, an optionally saturated cycloalkyl group, the alkyl, aryl, cycloalkyl groups optionally comprising one or more substituents selected from the group consisting of a halogen, an —$NO_2$ group a $C_{1-5}$ alkyl, a $C_{1-5}$ alkoxy, an optionally fused $C_{1-7}$ cycloalkyl, an optionally fused aryl group, optionally substituted by a halogen, a $C_{1-5}$ alkyl, and a $C_{1-5}$ alkoxy, the alkyl, cycloalkyl, aryl groups optionally comprising one or more heteroatoms; or A and B together form a $C_{2-6}$ substituted alkyl group, an optionally saturated $C_{3-9}$ cycloalkyl group, a $C_{5-10}$ aryl group, the groups optionally being substituted by a $C_{1-5}$ alkyl, a halogen, a hydroxy, a $C_{1-5}$ alkoxy, an amino, a sulfino, a sulfonyl, in which $R_4$ represents an alkyl, an alkoxy or an alkylcarbonyl, the alkyl, cycloalkyl, aryl groups optionally comprising one or more heteroatoms;

Q represents an oxygen, an —NR16, —NOR16 or —C(R16)$_2$ group, in which R16 is selected from the group consisting of a $C_{1-5}$ alkyl, an aryl group, and a heteroaryl group substituted by a $C_{1-4}$ alkyl.

18. A process for asymmetric hydrogenation of a compound of formula (XVI):

(XVI)

wherein

A and B are different and selected from among a $C_{1-5}$ alkyl group, an aryl group, a $C_{1-7}$ hydroxycarbonyl group, a $C_{1-7}$ alkoxycarbonyl group, a $C_{1-10}$ aryloxycarbonyl group, a $C_{1-7}$ halogenoalkyl group, a heteroaryl group, an optionally saturated cycloalkyl group, the alkyl, aryl, cycloalkyl groups optionally comprising one or more substituents selected from the group consisting of a halogen, an —$NO_2$ group a $C_{1-5}$ alkyl, a $C_{1-5}$ alkoxy, an optionally fused $C_{1-7}$ cycloalkyl, an optionally fused aryl group, optionally substituted by a halogen, a $C_{1-5}$ alkyl, and a $C_{1-5}$ alkoxy, the alkyl, cycloalkyl, aryl groups optionally comprising one or more heteroatoms; or A and B together form a $C_{2-6}$ substituted alkyl group, an optionally saturated $C_{3-9}$ cycloalkyl group, a $C_{5-10}$ aryl group, the groups optionally being substituted by a $C_{1-5}$ alkyl, a halogen, a hydroxy, a $C_{1-5}$ alkoxy, an amino, a sulfino, a sulfonyl, in which $R_4$ represents an alkyl, an alkoxy or an alkylcarbonyl, the alkyl, cycloalkyl, aryl groups optionally comprising one or more heteroatoms;

Q represents an oxygen, an —NR16, —NOR16 or —C(R16)$_2$ group, in which R16 is selected from the group consisting of a $C_{1-5}$ alkyl, an aryl group, and a heteroaryl group substituted by a $C_{1-4}$ alkyl, comprising treating the compound of formula (XVI) in a solvent in the presence of a complex according to claim 2.

19. The process according to claim 18, wherein the operating conditions are as follows:

at a temperature between 0 and +150° C., a hydrogen pressure between 1 and 100 bar, and an amount of catalyst in relation to an amount of compound of formula (XVI) is between 1/50,000 and 1/10.

20. The process according to claim 18, wherein the duration of hydrogenation is equal to or greater than 1 hour.

21. The process according to claim 18, wherein the concentration of the compound of formula (XVI) in the solvent is between 0.1 and 2 moles/liter.

* * * * *